US008460250B2

(12) United States Patent
Imai

(10) Patent No.: US 8,460,250 B2

(45) Date of Patent: Jun. 11, 2013

(54) MEDICAL CONTAINER

(75) Inventor: Masaomi Imai, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 742 days.

(21) Appl. No.: 12/666,468

(22) PCT Filed: Mar. 31, 2008

(86) PCT No.: PCT/JP2008/056390

§ 371 (c)(1), (2), (4) Date: Dec. 23, 2009

(87) PCT Pub. No.: WO2009/001600

PCT Pub. Date: Dec. 31, 2008

(65) Prior Publication Data

US 2010/0204658 A1 Aug. 12, 2010

(30) Foreign Application Priority Data

Jun. 26, 2007 (JP) ................................ 2007-167868

(51) Int. Cl.
*A61M 5/315* (2006.01)

(52) U.S. Cl.
USPC .......................................................... 604/220

(58) Field of Classification Search
USPC .......................................... 604/218–222, 230
See application file for complete search history.

(56) References Cited

U.S. PATENT DOCUMENTS

| | | | | |
|---|---|---|---|---|
| 5,090,961 | A * | 2/1992 | Maruzik et al. | 604/110 |
| 5,607,400 | A * | 3/1997 | Thibault et al. | 604/230 |
| 6,224,577 | B1 * | 5/2001 | Dedola et al. | 604/218 |

FOREIGN PATENT DOCUMENTS

| | | | |
|---|---|---|---|
| CH | 329581 | A | 6/1958 |
| JP | 3211223 | B2 | 9/2001 |
| JP | 3296025 | B2 | 6/2002 |
| JP | 2004-344639 | A | 12/2004 |
| JP | 2005-261931 | A | 9/2005 |

OTHER PUBLICATIONS

International Search Report for PCT/JP2008/056390 completed Apr. 23, 2008.
Written Opinion for PCT/JP2008/056390 completed Apr. 23, 2008.

* cited by examiner

*Primary Examiner* — Kevin C Sirmons
*Assistant Examiner* — Andrew Gilbert
(74) *Attorney, Agent, or Firm* — Buchanan Ingersoll & Rooney PC

(57) ABSTRACT

A medical container including a gasket. Before liquid is injected and discharged (first state), sufficient air-tightness and liquid-tightness are maintained by strong force of fitting of an elastic ring member, fitted on a large diameter part of a gasket body member, relative to a circular tube body. When liquid is injected and discharged (second state), which is a state in which the elastic ring member has been slid from the large diameter part of the gasket body member to a position where the elastic ring member is fitted on the small diameter part of the gasket body member, the fitting force of the elastic ring member, fitted on the small diameter part of the gasket body member, relative to the circular tube body is smaller than the fitting force before liquid is injected and discharged (first state). The construction reduces sliding resistance of the gasket against the circular tube body.

11 Claims, 15 Drawing Sheets

7
2
74
73
721
72
71
82
81
8
75

MEDICAL CONTAINER

TECHNICAL FIELD

The present invention relates to a syringe, particularly to a syringe in which sliding resistance between a gasket and the inside surface of a circular tube body is set to be great before injection and discharge of a liquid and be small at the time of injection and discharge of the liquid, while maintaining air-tightness and liquid-tightness inside the syringe.

BACKGROUND ART

While vials and ampules have been used as medical containers for a long time, prefilled syringes having an injection container preliminarily filled with a medical liquid have been developed in recent years. Particularly, prefilled syringes made of plastic which are unbreakable, light in weight and excellent in disposability have come to be widely used. The prefilled plastic syringe has a circular tube body, a gasket and a plunger, and is used after an injection needle having a diametric size suited to use is selectively connected to a tip of the circular tube body (in some cases, the injection needle is preliminarily installed). Such a syringe is designed taking into account its air-tightness and liquid-tightness so that the medical liquid contained therein is prevented from evaporating to the outside.

Furthermore, in order to prevent the medical liquid from leaking through a gap between the circular tube body and the gasket under an overwhelming injection resistance at the time of injecting the liquid into a living body, the syringe is designed taking into account also the air-tightness and liquid-tightness in the condition where an internal pressure is exerted.

On the other hand, for such a syringe to function, the gasket must be slid smoothly relative to the above-mentioned circular tube body. Thus, the contact surface is subjected to coating with a lubricant, a surface treatment or the like, if necessary.

As has been mentioned above, the medical containers having a contact surface between a gasket and a circular tube body such as a prefilled syringe are rigorously designed so as to simultaneously fulfill the two contradictory functions, namely, the air-tightness and liquid-tightness, and the slidability of the gasket relative to the circular tube body. However, the currently achievable slidability may be insufficient, in the case where a tiny amount of a medical liquid is injected by use of a syringe pump, or depending on the kind of the medical liquid or the capacity of the syringe.

In view of this, there has been proposed a method for reducing the sliding resistance by reducing the outside diameter of the gasket immediately before use (Patent Documents 1 and 2). According to this method, a medical container capable of reducing the sliding resistance between a syringe outer tube and a gasket immediately before use has been disclosed.

The above-mentioned prior art, however, has problems on the basis of manufacture and use which are yet to be solved. Normally, in the manufacture of a prefilled syringe, a plunger is mounted to a gasket inside a syringe outer tube in a final step. This is because if the plunger were mounted before a filling step, the plunger would obstruct the filling operation. In the case of Patent Document 1, the gasket is pressed against the syringe outer tube by a tip portion of the plunger. Before the plunger is mounted, therefore, the size of a screw hole in the gasket inside the syringe outer tube is necessarily smaller than the screw diameter of the plunger. This results in that it may be difficult to mount the plunger to the gasket in the syringe outer tube. In other words, the manufacturing method for the syringe is limited to a method in which the plunger is mounted to the gasket and thereafter this assembly is inserted into the syringe outer tube.

In addition, the prefilled syringes include those which are sold in the state in which a syringe outer tube portion and a plunger portion are separate from each other, so as to enhance ease of containment of these components into a packaging. In this case, like in the above-mentioned case, because the size of the screw hole in the gasket present inside the syringe outer tube is smaller than the screw diameter of the plunger, again, it is difficult to mount the plunger.

On the other hand, FIGS. 9 and 10 in Patent Document 2 show the use of a slit-rib combination instead of the screw fit. This approach also fails to simultaneously realize operability in inserting the plunger into the gasket and prevention of the plunger from falling off in use. In other words, like in the above-mentioned cases, in order to easily insert the plunger into the gasket present inside the syringe outer tube, there must be a dimensional relation such that the ribs of the plunger are comparatively loosely fitted in the slits formed in the gasket.

After the insertion, the syringe can be stored in the state in which the plunger has been rotated so as to enhance the adhesion between the gasket and the syringe outer tube. When the plunger is rotated in use, the syringe is returned into the state where the adhesion between the gasket and the syringe outer tube is low. Then, the plunger may easily fall off to the hand side because of the loose initial fit between the slits formed in the gasket and the ribs of the plunger.

Patent Document 1: Japanese Patent No. 3211223

Patent Document 2: Japanese Patent No. 3296025

DISCLOSURE OF INVENTION

An object of the present invention is to provide a medical container including a gasket which fulfills easily the air-tightness and liquid-tightness necessary for a syringe and the slidability of a gasket relative to a circular tube body.

In order to achieve the above object, according to the present invention, there is provided a medical container including a circular tube body, and a cylindrical gasket slidable inside the circular tube body in an air-right and/or liquid-tight manner, with a liquid passage formed on the tip side through the circular tube body or the gasket, wherein the gasket is composed of a gasket body member having a cylindrical outside shape, and an elastic ring member fitted on the gasket body member, the gasket body member has a fitting portion for fitting in the elastic ring member, the fitting portion having a large diameter part and a small diameter part, an inside diameter of the elastic ring member is smaller than the large diameter part in a natural state, while an outside diameter of the elastic ring member is larger than an inside diameter of the circular tube body in a state where the elastic ring member is fitting on the large diameter part, and the elastic ring member is fitted onto the small diameter part in a second state by sliding the gasket in a longitudinal axial direction from a first state in which the elastic ring member is fitted on the large diameter part inside the circular tube body.

This ensures that sufficient air-tightness and liquid-tightness are maintained before liquid is injected and discharged (first state). When the liquid is injected and discharged (second state), a fitting force of the elastic ring member, which is fitted over the gasket body member, relative to the circular tube body is reduced, whereby the sliding resistance in sliding of the gasket relative to the circular tube body is reduced (gasket slidability satisfactory for use is developed). As a result, a medical container including a gasket which can exhibit excellent slidability while maintaining air-tightness and liquid-tightness can be provided. Since the fitting force is reduced, a higher slidability of the gasket at the time of injection and discharge of liquid (second state) is more favorable, and the sliding resistance at the time of injection and discharge of the liquid (second state) is preferably 0.01 to 50 N, more preferably 0.01 to 10 N.

In addition, in the medical container according to the present invention, preferably, in the first state, an outer circumferential portion of the elastic ring member and an inside surface of the circular tube body make contact with each other on the circumference.

With this structure, the air-tightness and liquid-tightness necessary for a syringe and the slidability of the gasket relative to the circular tube body are easily fulfilled.

Further, in the medical container according to the present invention, preferably, a fitting force between the outer circumferential portion of the elastic ring member and the inside surface of the circular tube body is greater in the first state than in the second state.

This ensures that the elastic ring member in the first state is assuredly brought into the second state by the movement of the gasket body member relative to the circular tube body along the longitudinal axial direction of the circular tube body.

In addition, in the medical container according to the present invention, preferably, the outer circumferential portion of the gasket body member has at least one peak which extends continuously and which makes contact with the circular tube body in an air-tight and/or liquid-tight manner.

This makes it possible to maintain air-tightness and liquid-tightness of the inside of the medical container.

Further, in the medical container according to the present invention, preferably, an outside surface of the gasket body member and/or the inner circumference of the elastic ring member has been coated with a lubricant or subjected to a surface treatment.

This ensures easy sliding of the elastic ring member on the large diameter part.

In addition, in the medical container according to the present invention, preferably, sliding resistance between the elastic ring member and the gasket body member is smaller than sliding resistance between the elastic ring member and the circular tube body.

This ensures that the elastic ring member in the first state is assuredly brought into the second state by the movement of the gasket body member relative to the circular tube body along the longitudinal axial direction of the circular tube body.

Further, in the medical container according to the present invention, preferably, the large diameter part is located on the base end side relative to the small diameter part, and the elastic ring member in the first state is brought into the second state by movement of the gasket body member in a direction toward a base end relative to the circular tube body.

This ensures that the elastic ring member in the first state is brought into the second state assuredly.

In addition, in the medical container according to the invention, preferably, the large diameter part is located on the tip side relative to the small diameter part, and the elastic ring member in the first state is brought into the second state by movement of the gasket body member in a direction toward a tip relative to the circular tube body.

This ensures that the elastic ring member in the first state is assuredly brought into the second state.

Further, in the medical container according to the present invention, preferably, the elastic ring member has a portion which is compressed between the gasket body member and the circular tube body in the first state.

This makes it possible to maintain the air-tightness and liquid-tightness of the inside of the medical container.

In addition, in the medical container according to the present invention, preferably, the elastic ring member has an engaging portion for engagement with a boundary portion between the large diameter part and the small diameter part.

This makes it possible to prevent the elastic ring member in the first state from being moved involuntarily toward the opposite side from the small diameter part.

Further, in the medical container according to the present invention, preferably, the elastic ring member is out of contact with the circular tube body in the second state.

This reduces the sliding resistance in sliding of the gasket relative to the circular tube body.

In addition, the medical container according to the present invention, preferably, is preliminarily filled with a medicine.

This ensures that at the time of using the medical container, the work can be done speedily.

BEST MODE FOR CARRYING OUT THE INVENTION

Figure 1:
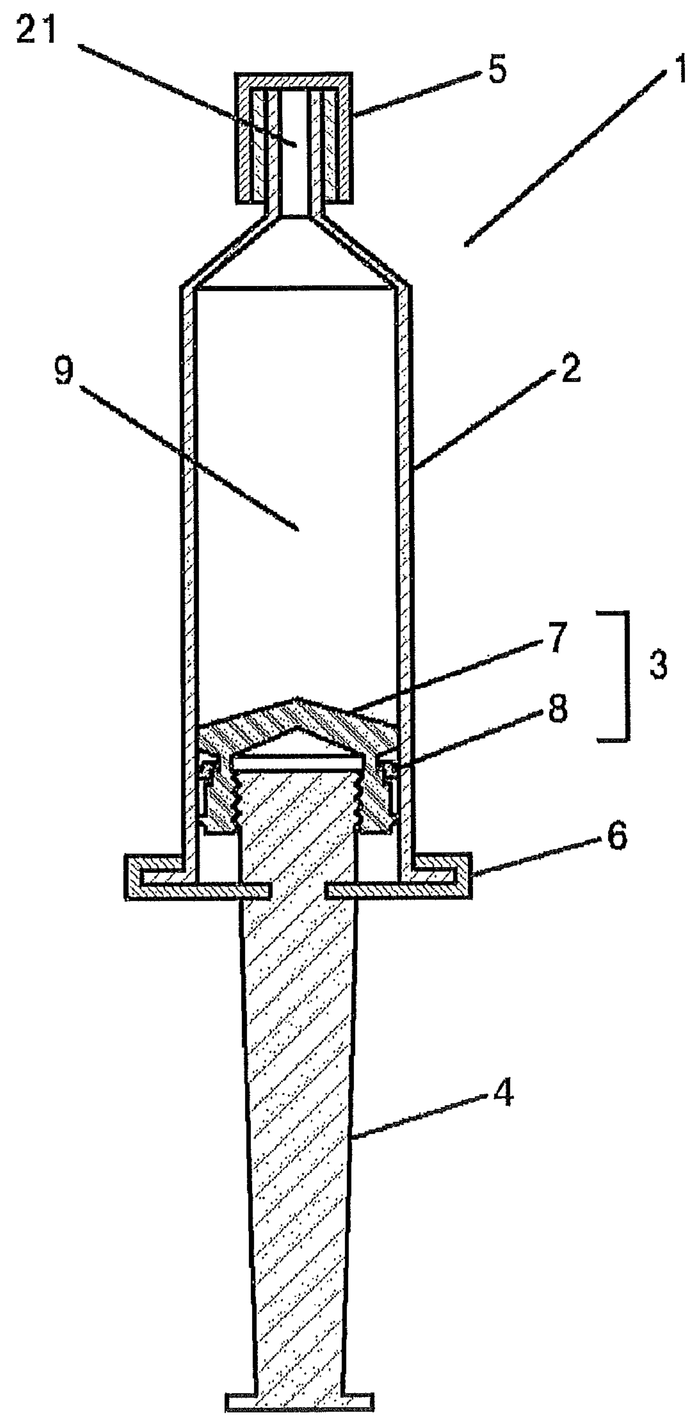
FIG. 1 is a sectional view of a prefilled syringe according to Embodiment 1 before liquid is injected and discharged (first state).

The medical container according to the present invention will be described below referring to the drawings.

Embodiment 1

FIGS. 1 to 7 show a prefilled syringe 1 which is an exemplary embodiment of the present invention. In the following, for convenience of explanation, the upper side in FIGS. 1 to 3 and FIGS. 6 and 7 (and in FIGS. 8 to 13 as well) will be referred to as "distal" and the lower side as "proximal," and the left side in FIG. 5 will be referred to as "distal" and the right side as "proximal."

FIG. 1 shows the prefilled syringe 1 before liquid is injected and discharged (first state). The prefilled syringe 1 includes a circular tube body 2, a gasket 3, a plunger 4, a tip cap 5, and plunger position restricting means 6. The gasket 3 includes a gasket body member 7 having a cylindrical outside shape, and an elastic ring member 8. A medical liquid is contained (preserved) in a space 9 surrounded by the tip cap 5, the circular tube body 2, and the gasket body member 7.

The capacity of the prefilled syringe 1 is preferably 0.5 to 100 mL, more preferably 1 to 50 mL. In addition, the length of the circular tube body 2 is preferably 50 to 150 mm, more preferably 60 to 125 mm.

The tip cap 5 is disposed as sealing means for maintaining air-tightness and liquid-tightness of a distal portion of the circular tube body 2. The sealing means may not necessarily be a cap, and may be a sheet member used for sealing.

The gasket body member 7 is provided at part of its outer periphery with a fitting portion 71 reduced in diameter. The fitting portion 71 of the gasket body member 7 includes a large diameter part 72 on the rear end side (proximal side) and a small diameter part 73 on the distal side. On the fitting portion 71, the elastic ring member 8 is slidably fitted in a range from the large diameter part 72 to the small diameter part 73. In addition, the gasket body member 7 has a first peak 74 and a second peak 75. The first peak 74 is disposed primarily for maintaining air-tightness and liquid-tightness, while the second peak 75 is disposed primarily for preventing the gasket 3 from being inclined.

The shape of the elastic ring member 8 is not limited as long as the elastic ring member 8 in the state of being fitted on the large diameter part 72 (first state) has a ring shape which is the same as the circumference of the inside surface of the circular tube body 2; in the condition of not being fitted on the large diameter part 72 (second state), the elastic ring member 8 may be an O-ring, D-ring or the like.

Figure 5:
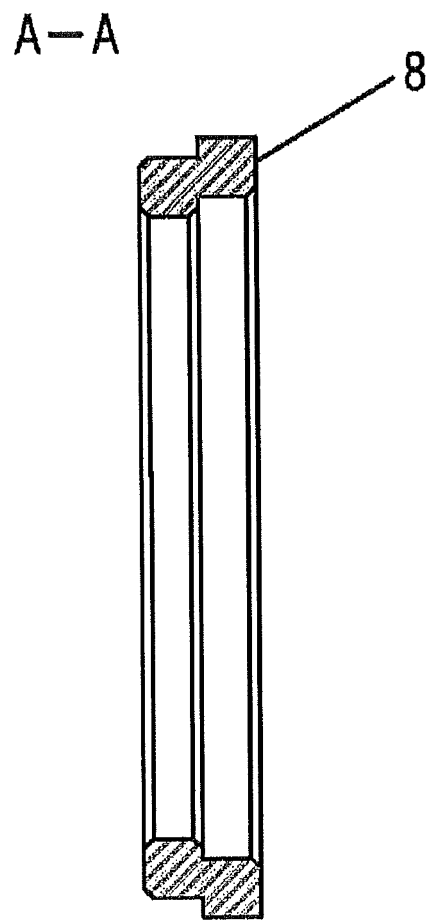
FIG. 5 is a sectional view (sectional view taken along line A-A of FIG. 4) of the elastic ring member.

FIG. 5 is a sectional view (sectional view taken along line A-A of FIG. 4) of the elastic ring member 8. While the elastic ring member 8 in the present embodiment has a Z-shaped cross section which fits suitably onto the large diameter part 72 and the small diameter part 73, the sectional shape may be a circle, a triangle, a quadrilateral, an L-shape, a concave, a convex, a star shape or the like insofar as air-tightness and liquid-tightness can be maintained.

In the state before the liquid is injected and discharged (first state), the elastic ring member 8 is fitted on the large diameter part 72 of the fitting portion 71. In this instance, the elastic ring member 8 is pressed by the gasket body member 7 into the state of being enlarged radially outwards, since the inside diameter of the elastic ring member 8 is set to be smaller than the outside diameter of the large diameter part 72. This ensures that the elastic ring member 8 firmly presses against the inside surface of the circular tube body 2, whereby high air-tightness and liquid-tightness can be maintained, and evaporation of a medical liquid can be effectively prevented.

In the state before the liquid is injected and discharged (first state), the fitting force between the inside surface of the circular tube body 2 and the elastic ring member 8 is greater than the fitting force between the elastic ring member 8 and the large diameter part 72. With this structure, the sliding resistance between the elastic ring member 8 and the large diameter part 72 (the gasket body member 7) is smaller than the sliding resistance between the elastic ring member 8 and the circular tube body. Consequently, in an operation of pulling the plunger 4 rearwards, the elastic ring member 8 in the first state is not moved rearwards together with the gasket body member 7 but is released from fit on the large diameter part 72 of the gasket body member 7, namely, the elastic ring member 8 is released from the large diameter part 72 of the gasket body member 7. Accordingly, the elastic ring member 8 is moved onto the small diameter part 73, assuredly resulting in the second state.

The inside diameter of the elastic ring member 8 fitted on the large diameter part 72 of the gasket body member 7 and the inside diameter of the elastic ring member 8 fitted on the small diameter part 73 are preferably 1.2 to 48 mm and 1.1 to 47 mm, more preferably 1.4 to 28 mm and 1.3 to 27 mm, respectively. Further, the outside diameter of the elastic ring member 8 put in contact with the inside surface of the circular tube body 2, in natural state, is preferably 1.95 to 50 mm, more preferably 3.9 to 30 mm.

The outside diameters of the large diameter part 72 and the small diameter part 73 of the gasket body member 7 in natural state are preferably 1.3 to 53 mm and 1 to 46 mm, more preferably 1.5 to 31 mm and 1.2 to 26 mm, respectively. The inside diameter of the circular tube body 2 in natural state is preferably 2 to 55 mm, more preferably 4 to 33 mm.

As for the difference between the outside diameter of the large diameter part 72 of the gasket body member 7 and the inside diameter of the elastic ring member 8 fitted thereon, it is preferable that the inside diameter of the elastic ring member 8 is smaller by 0.1 to 5 mm, more preferably by 0.1 to 3 mm. If the diameter difference is less than 0.1 mm, the elastic ring member 8 would easily be released from fitting on the gasket body member 7. If the diameter difference is more than 5 mm, deformation amount of the elastic ring member 8 would be so large that the release from fitting is unsuitably difficult to achieve.

In addition, as for the difference between the inside diameter of the circular tube body 2 and the outside diameter of the elastic ring member 8 put in contact therewith, it is preferable that the outside diameter of the elastic ring member 8 is smaller by 0.05 to 5 mm, more preferably by 0.1 to 3 mm.

In order to prevent the gasket 3 from being slid inadvertently, the plunger position restricting means 6 which can be fixed to a flange and through which the plunger 4 can be passed is mounted to a housing for the plunger 4.

In the form of a prefilled syringe to be used with the plunger 4 mounted immediately before liquid is injected and discharged, the plunger position restricting means 6 is not needed. When the gasket body member 7 and the elastic ring member 8 are assembled and thereafter the assembly is inserted into the circular tube body 2, the assembly can be contained easily and in a stable state, so that no inconvenience is caused on a manufacture basis.

Figure 2:
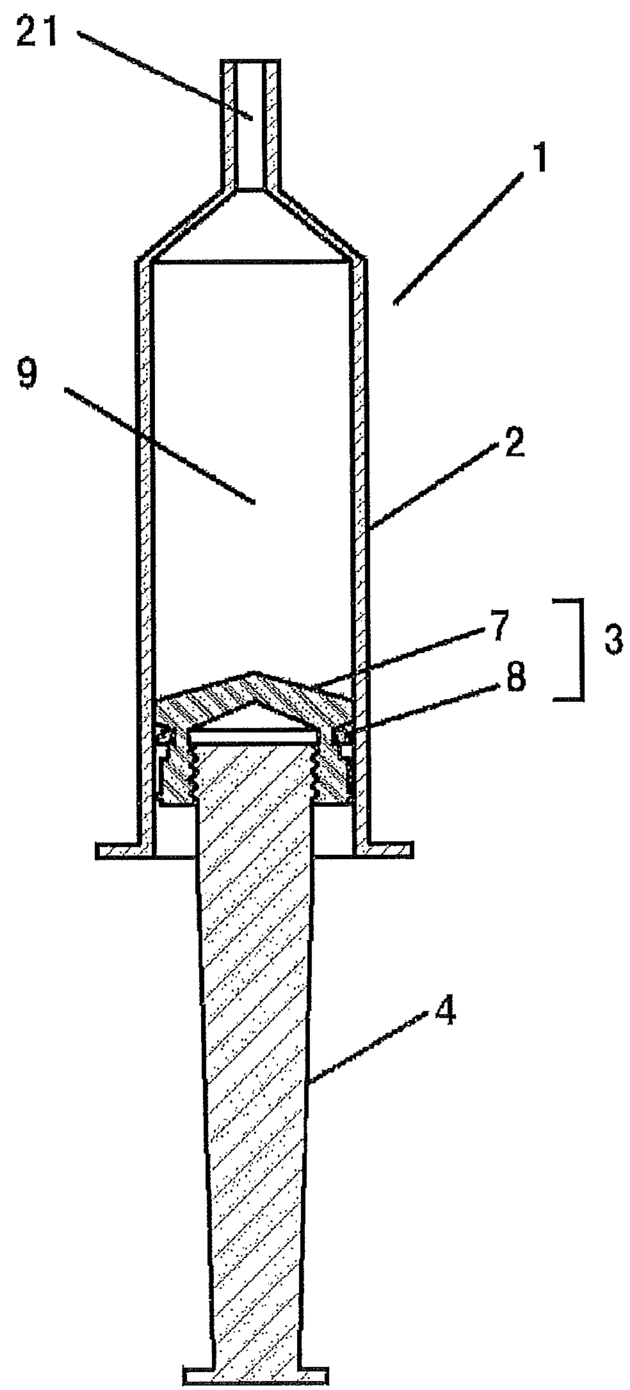
FIG. 2 is a sectional view of the prefilled syringe according to Embodiment 1 when the liquid is injected and discharged (second state).
Figure 3:
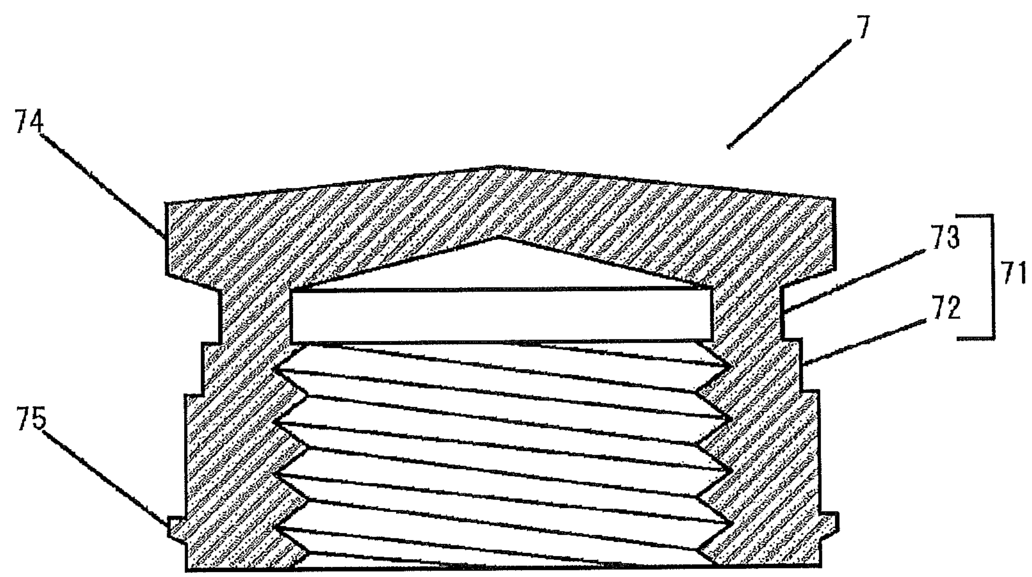
FIG. 3 is a sectional view of a gasket body member.
Figure 4:
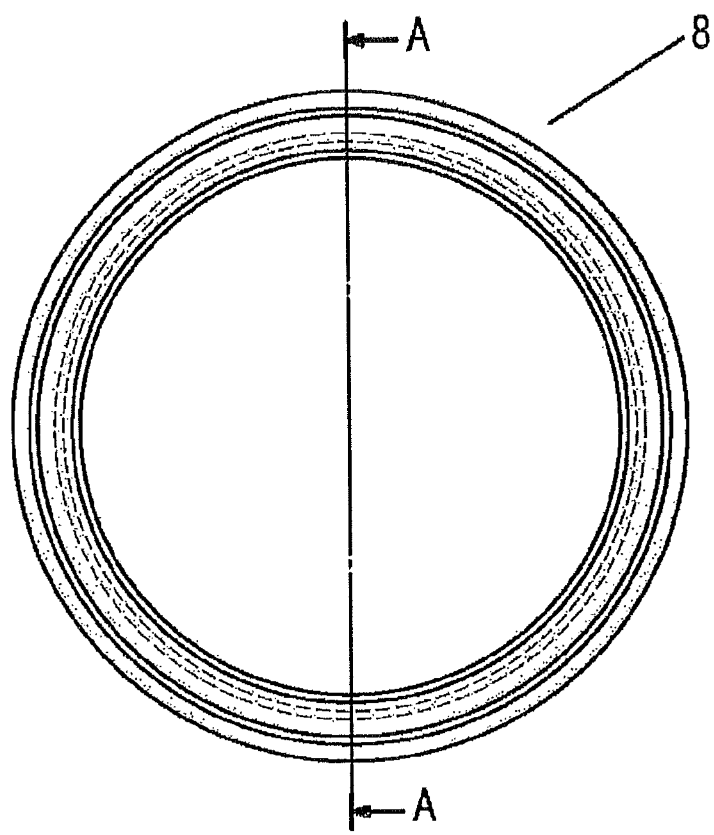
FIG. 4 is a plan view of an elastic ring member.

FIG. 2 shows the prefilled syringe 1 in the state at the time of injection and discharge of the liquid (second state).

When the plunger position restricting means 6 is removed and the plunger 4 is pulled, starting from the first state shown in FIG. 1, the gasket body member 7 is slightly slid toward the rear end side, generating a negative internal pressure. The elastic ring member 8 is enlarged by the pressure from the gasket body member 7 and is firmly fitted to the circular tube body 2, so that the gasket body member 7 cannot be slid easily.

In this instance, the fitting force between the inside surface of the circular tube body 2 and the elastic ring member 8 is stronger than the fitting force between the elastic ring member 8 and the large diameter part 72, so that the elastic ring member 8 is slid to a position where it is fitted on the small diameter part 73.

In addition, the Z-shaped cross section of the elastic ring member 8 ensures that, upon transition from the first state to the second state, the fitting between the elastic ring member 8 and the inside surface of the circular tube body 2 is released effectively.

Figure 6:
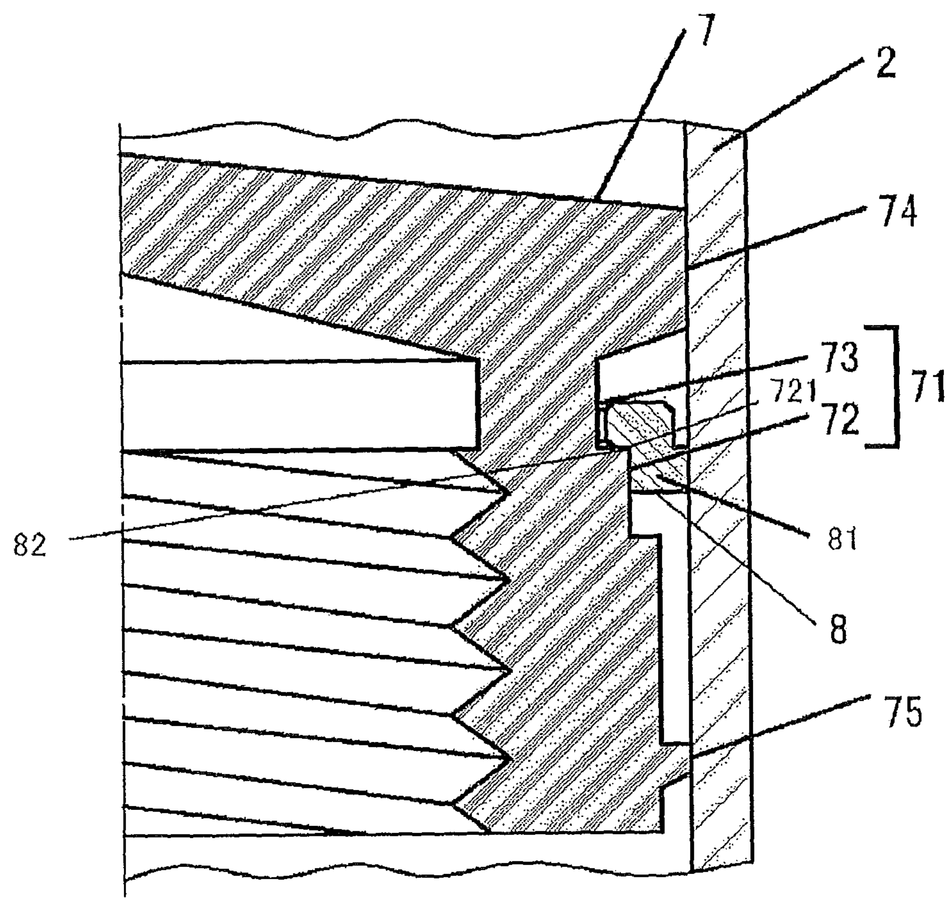
FIG. 6 is a sectional view showing the positional relationship between the gasket body member and the ring member according to Embodiment 1 before the liquid is injected and discharged (first state).

Further, as shown in FIG. 6, since the elastic ring member 8 has such a sectional shape as mentioned above, the elastic ring member 8 has a compressed portion 81 which is compressed between the outer circumferential surface of the large diameter part 72 of the gasket body member 7 and the inner circumferential surface of the circular tube body 2 in the first state. With the compressed portion 81, the air-tightness and liquid-tightness of the inside of the prefilled syringe 1 can be maintained securely.

In addition, the elastic ring member 8 having such a sectional shape has an engaging portion (stepped portion) 82 for engagement with a boundary portion (stepped portion) 721 between the large diameter part 72 and the small diameter part 73 in the first state. With the engaging portion 82, the elastic ring member in the first state can be prevented from being involuntarily moved toward the opposite side from the small diameter part 73, namely, in the rearward direction.

Application of a lubricant such as silicone oil to the large diameter part 72 facilitates sliding of the elastic ring member 8 on the large diameter part 72. In addition, coating the large diameter part 72 with a silicone or fluororesin facilitates sliding of the elastic ring member 8 on the large diameter part 72.

The sliding results in the second state in which the elastic ring member 8 is fitted on the small diameter part 73 of the gasket body member 7. Though not particularly limited, the sliding distance of the gasket body member 7 is preferably 0.3 to 15 mm, more preferably 1 to 5 mm. If the sliding distance is less than 0.3 mm, there is a risk of inadvertent sliding. If the sliding distance exceeds 15 mm, the overall length of the gasket 3 is enlarged, resulting in that the syringe as a whole is undesirably enlarged meaninglessly.

Since the outside diameter of the small diameter part 73 of the gasket body member 7 is smaller than the outside diameter of the large diameter part 72, the deformation of the elastic ring member 8 having been enlarged radially outwards by pressure is lost or reduced. In other words, the fitting force between the inside surface of the circular tube body 2 and the elastic ring member 8, or the fitting force between the inside surface of the circular tube body 2 and the gasket 3, in the second state is weaker than the fitting force in the first state. Especially, in this embodiment, the outer circumferential surface of the elastic ring member 8 in the second state is out of contact with the inner circumferential surface of the circular tube body 2 (see FIG. 7).

Consequently, when the tip cap 5 is removed and the plunger 4 is pushed, the gasket 3 is slid as an ordinary gasket, with the elastic ring member 8 remaining located on the small diameter part 73 of the gasket body member 7 in an integral manner. In other words, the sliding resistance in sliding of the gasket 3 relative to the circular tube body 2 is reduced, and injection and discharge of the medical liquid can be carried out smoothly. The air-tightness and liquid-tightness in this instance is maintained by the first peak 74 of the gasket body member 7.

Examples of the material for the gasket body member 7 include styrene-based elastomers, silicone rubbers, and butyl rubbers and the like.

In addition, examples of the material of the circular tube body 2 include polypropylene, cyclic polyolefins, and polycarbonate.

For the elastic ring member 8, the same materials as those for the gasket body member 7 can be used. However, since the elastic ring member 8 is to be deformed by the gasket body member 7, it is preferable that a material more liable to be deformed than the material of the gasket body member 7 is selected for the elastic ring member 8. In the case where the material of the elastic ring member 8 is not more liable to be deformed than the material of the gasket body member 7, it is possible to meet the requirement by adopting a design (e.g., shape or material thickness) of the elastic ring member 8 for easy deformation.

While a structure wherein the gasket body member 7 is slid by pulling the plunger 4 is adopted in this embodiment, the sliding may be effected by exerting a pressure by injecting a medical liquid or the like via a liquid passage 21 in the circular tube body.

Embodiment 2

Figure 8:
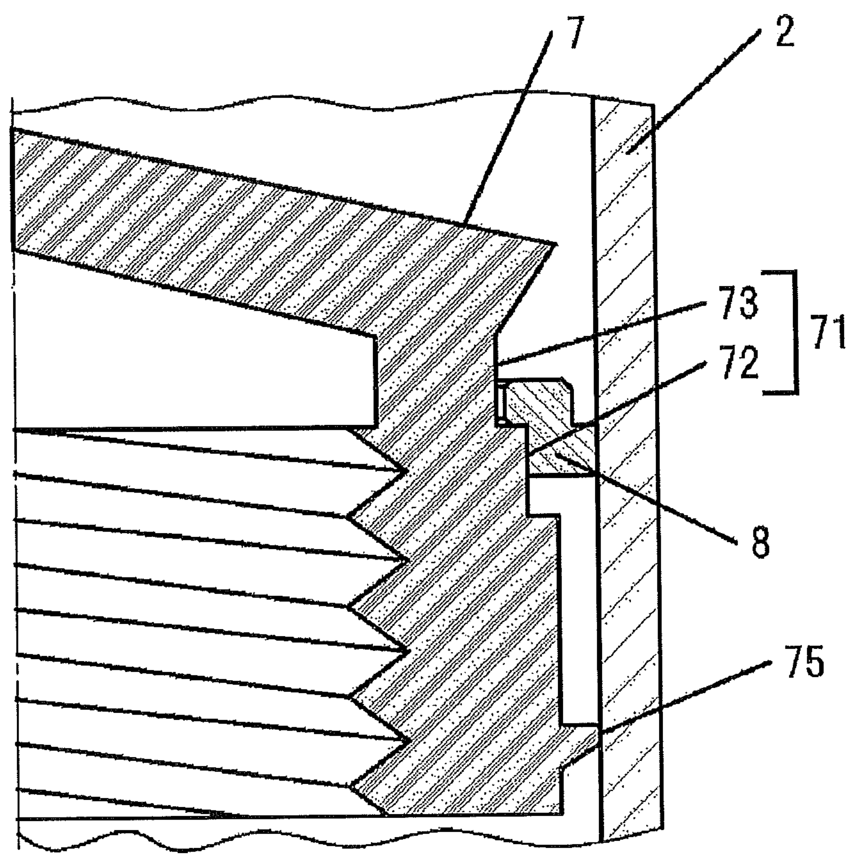
FIG. 8 is a sectional view showing the positional relationship between a gasket body member and a ring member according to Embodiment 2 before liquid is injected and discharged (first state).
Figure 9:
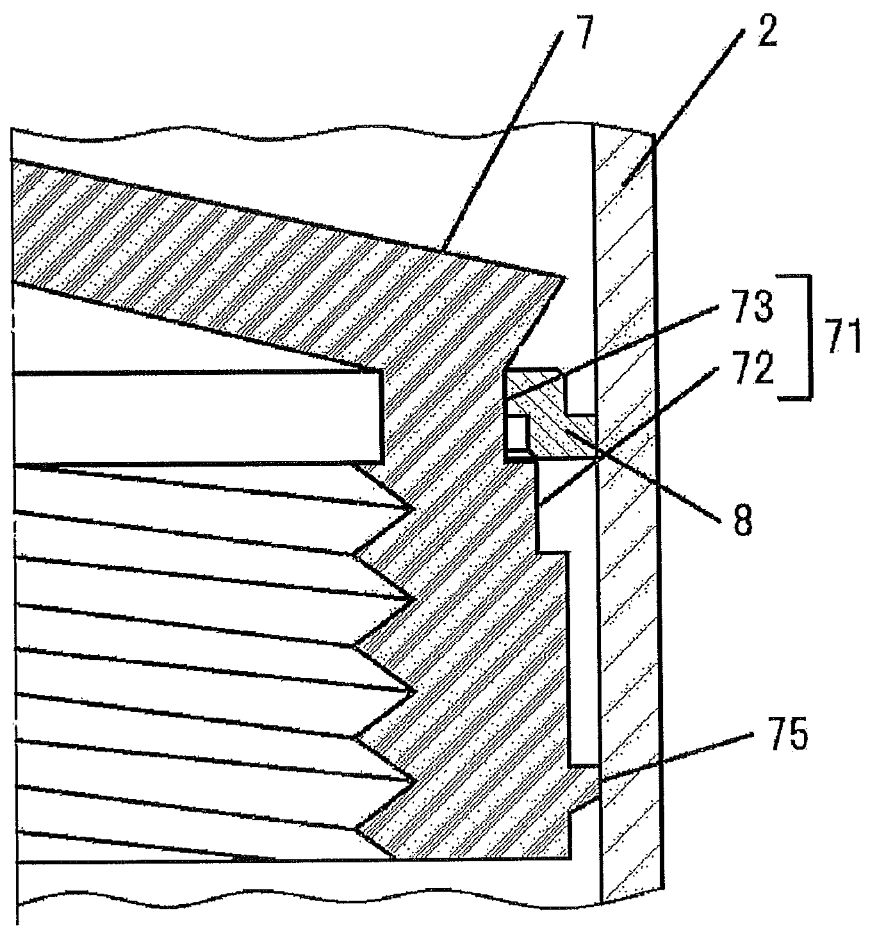
FIG. 9 is a sectional view showing the positional relationship between the gasket body member and the ring member according to Embodiment 2 when the liquid is injected and discharged (second state).

FIGS. 8 and 9 show Embodiment 2.

In this embodiment, the configuration of a prefilled syringe is the same as in Embodiment 1, except that an elastic ring member 8 functions also as a first peak of a gasket. Therefore, the following explanation will focus on the difference in configuration. FIG. 8 shows the positional relationship between a gasket body member 7 and the elastic ring member 8 in the first state, and FIG. 9 shows the positional relationship between the gasket body member 7 and the elastic ring member 8 in the second state.

In this embodiment, the gasket body member 7 and the elastic ring member 8 are accommodated in a circular tube body 2. In the first state, a large diameter part 72 of a fitting portion 71 of the gasket body member 7 is fitted in an inside diameter circumferential portion of the elastic ring member 8. Further, in this embodiment, the elastic ring member 8 functions also as the first peak of the gasket, so that the elastic ring member 8 is preferably thicker than the elastic ring member 8 in Embodiment 1.

In the first state, air-tightness and liquid-tightness is maintained by strong fitting between the inside surface of the circular tube body 2 and the elastic ring member 8, in the same manner as in Embodiment 1. Though a second peak 75 is present in the gasket body member 7, the first peak is not formed (omitted), and the elastic ring member 8 plays the role of the first peak.

Like in Embodiment 1, pulling a plunger 4 causes only the gasket body member 7 to be slid toward the rear end side, while the elastic ring member 8 is located onto a small diameter part 73 of the fitting portion 71, resulting in the second state. In this instance, the fitting force between the elastic ring member 8 and the circular tube body 2 is reduced, but the ring and the inside surface of the circular tube body remain in contact with each other. As a result, the sliding resistance in sliding of the gasket 3 relative to the circular tube body 2 is reduced, and injection and discharge of a medical liquid can be smoothly carried out, with the elastic ring member 8 playing the role of a peak.

While an embodiment in which the elastic ring member 8 plays the role of the first peak has been described in this embodiment, the second peak may be configured in the same way. In addition, both the first and second peaks may be configured in the same manner. Furthermore, in order to prevent the medical liquid from remaining in the vicinity of the elastic ring member 8, a third peak (the first peak 74 in Embodiment 1) or the like may be provided between a space 9 and the elastic ring member 8.

Embodiment 3

Figure 10:
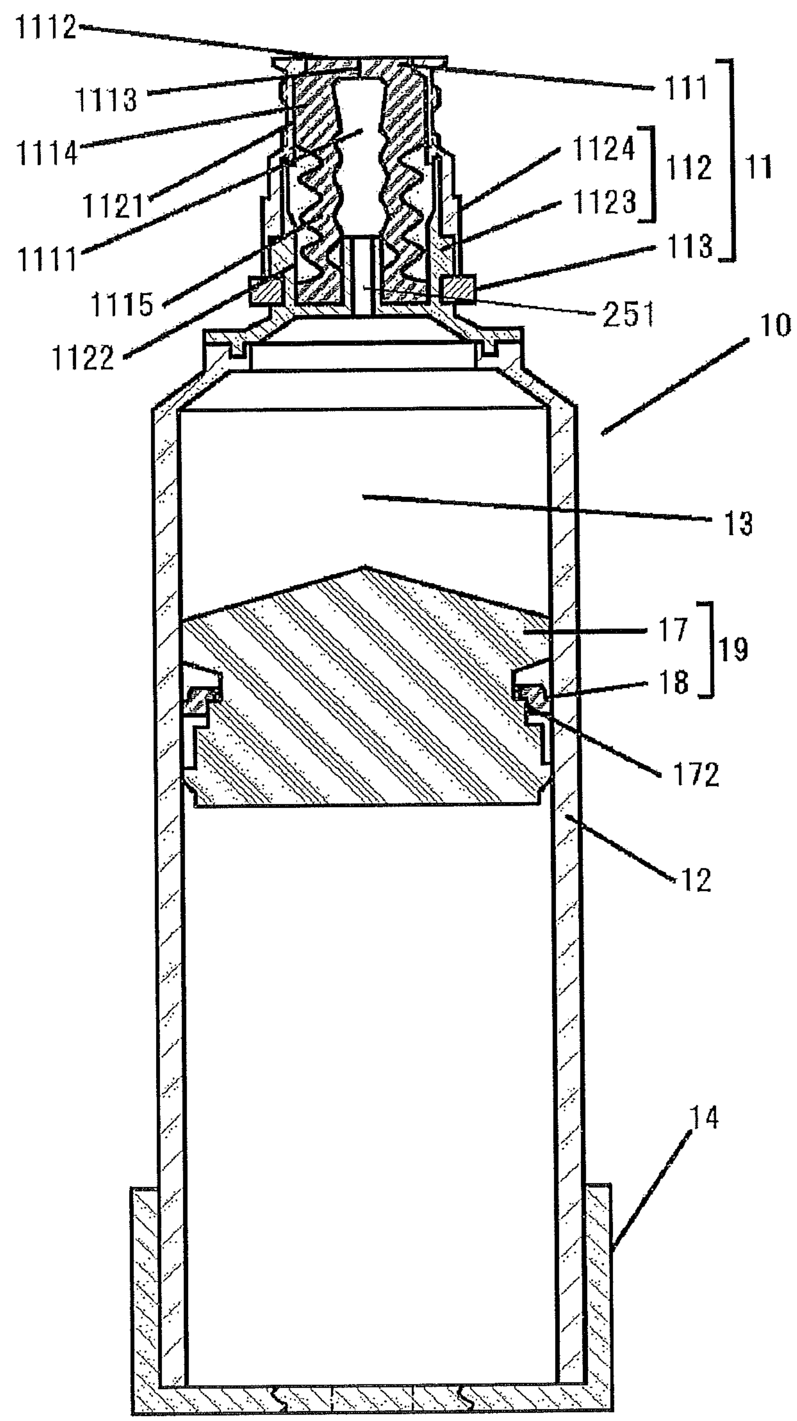
FIG. 10 is a sectional view of a powdery preparation container according to Embodiment 3.
Figure 11:
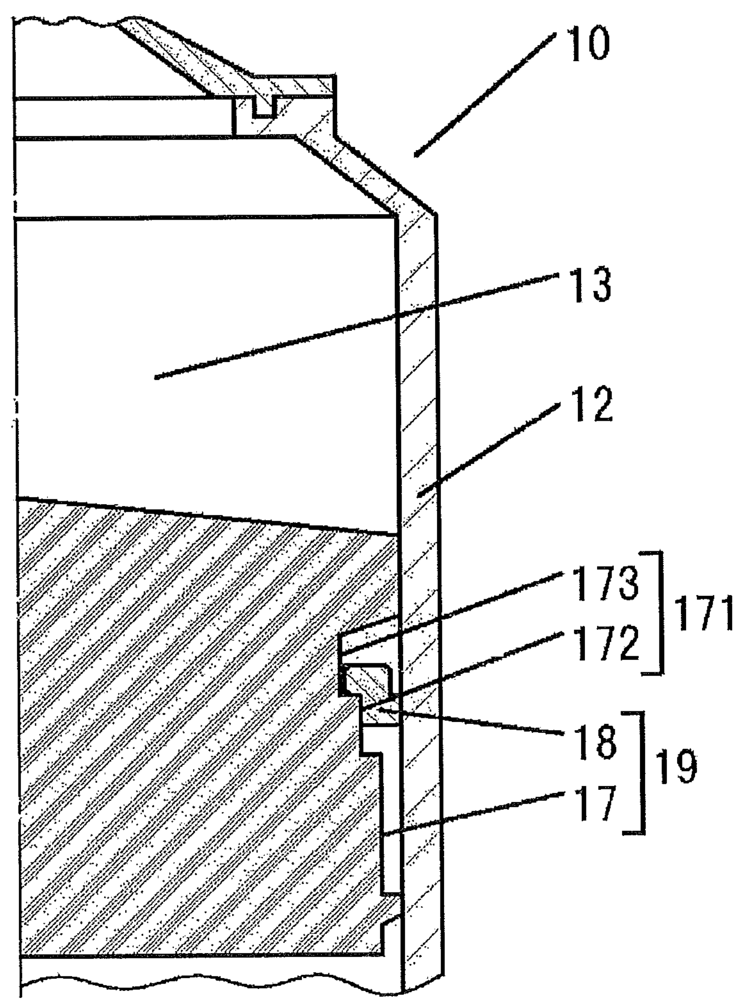
FIG. 11 is a sectional view showing the positional relationship between a gasket body member and a ring member according to Embodiment 3 before liquid is injected and discharged (first state).
Figure 12:
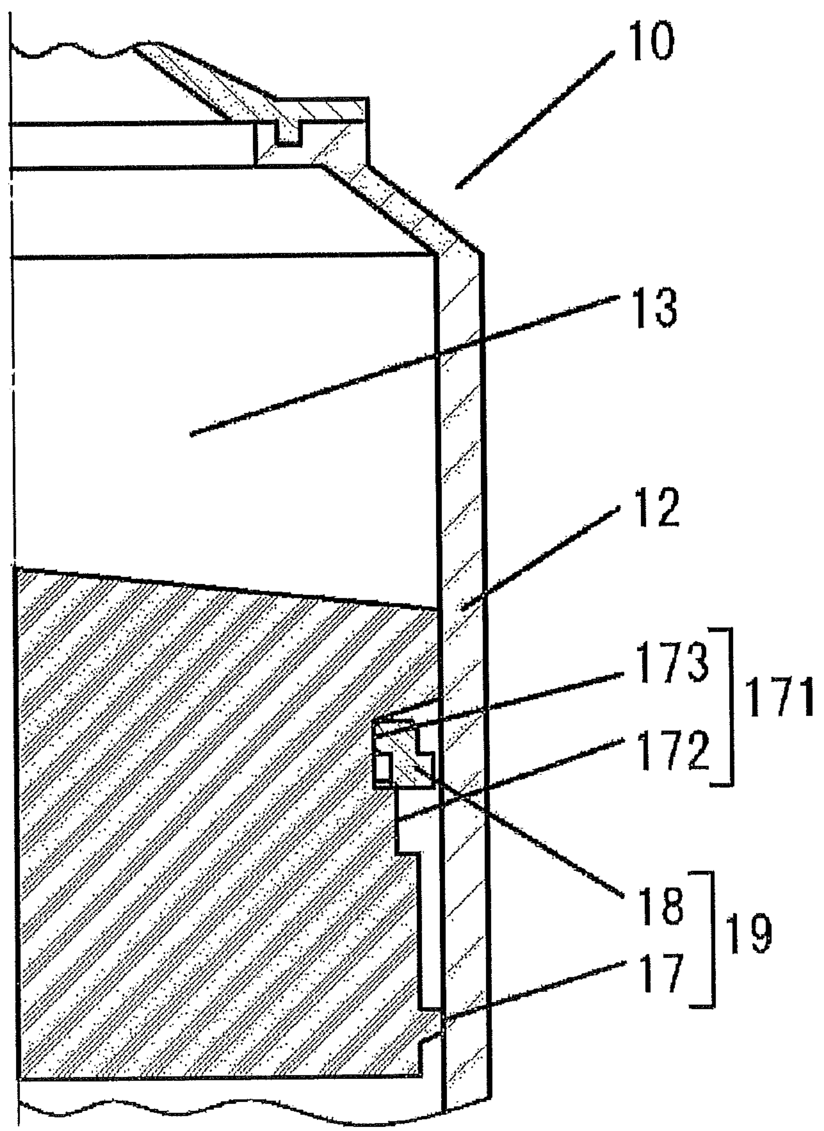
FIG. 12 is a sectional view showing the positional relationship between the gasket body and a ring member according to Embodiment 3 when the liquid is injected and discharged (second state).

FIGS. 10 to 12 show a powdery preparation container 10 which is an exemplary embodiment of the present invention.

The powdery preparation container 10 includes a circular tube body 12, a gasket 19, a connector 11, and a rear end cap 14. A powdery preparation is contained in a powdery preparation containing part 13. A liquid passage 251 in the powdery preparation container 10 is the connector 11 which can be connected to the distal end of a syringe or the like.

The connector 11 is not particularly limited, and examples thereof include the one described in Japanese Laid-Open Patent Publication No. 2005-261931. In this embodiment, the connector disclosed in Japanese Laid-open Patent Publication No. 2005-261931 is used. Specifically, the connector 11 includes a valve body 111 which has a liquid flowing part 1111 formed from an elastic material and permitting a liquid to pass therethrough, a head part 1114 formed with a slit 1113 extending from a flat top surface 1112 up to the liquid flowing part 1111, and a barrel part 1115; and a housing 112 having a first inner cavity 1121, into which the head part 1114 is insertable, and a second inner cavity 1122 communicating with the first inner cavity 1121 and having an inner diameter larger than that of the first inner cavity 1121. The housing 112 includes a housing body 1123, and a cover (cap) 1124. The air-tightness at the boundary between the housing body 1123 and the cover 1124 is maintained by an O-ring 113.

The head part 1114 has a tapered portion such that the outside diameter in the vicinity of the top surface 1112 gradually increases toward the barrel part 1115. When a pipe body (male connector) is not connected, the head part 1114 is inserted in the first inner cavity 1121, with the slit 1113 closed. When a pipe body is connected, the pipe body presses the top surface 1112 of the head part 1114, whereby the head part 1114 is brought into the second inner cavity 1122, and the slit 1113 deforms together with the head part 1114, to be opened.

The gasket 19 including the gasket body member 17 and the elastic ring member 18 is contained in the circular tube body 12.

Further, in this embodiment, the materials for the circular tube body 12, the gasket body member 17 and the elastic ring member 18 are the same as those in Embodiment 1.

In FIG. 10, the first state is shown in which a large diameter part 172 of the gasket body member 17 is fitted in the elastic ring member 18.

In this instance, air-tightness and liquid-tightness is offered by strong fitting between the inside surface of the circular tube body 12 and the elastic ring member 18 (FIG. 11), in the same manner as in Embodiment 1.

Next, a syringe (not shown) filled with a dissolving liquid is connected to the connector 11, and a plunger of the syringe is pushed, whereby the dissolving liquid in the syringe is caused to flow into the powdery preparation container 10.

In this instance, as shown in FIG. 12, only the gasket body member 17 is slid toward the rear end side, resulting in the second state in which the elastic ring member 18 is located on a small diameter part 173. In other words, the elastic ring member 18 is reduced in outside diameter. As a result, the fitting force between the elastic ring member 18 and the inside surface of the circular tube body 12 is reduced, and the sliding resistance in sliding of the gasket 19 relative to the inside surface of the circular tube body 12 is reduced. Therefore, the gasket 19 is easily slid toward the rear end side, while the dissolving liquid is flowing in. Thereafter, a medical liquid formed upon dissolution of the powdery preparation in the dissolving liquid can be easily recovered into the syringe, in which the dissolving liquid has been contained, by pulling the plunger.

While a container for a powdery preparation has been described as an example in this embodiment, the medicine contained in the container may be any of various forms such as liquid preparation, powdery preparation, tablet, and jelly preparation. In the case where the medicine contained is a liquid preparation or a jelly preparation or the like, evaporation of the contained medicine to the exterior of the container can be prevented. In the case where the medicine contained is a powdery preparation, as in this embodiment, or tablets or the like, moistening of the medicine through penetration of moisture can be restrained.

In addition, while an embodiment in a normal-pressure condition as in Embodiment 1 has been described in this embodiment, a reduced-pressure condition may also be adopted.

Furthermore, a rear end cap 14 may be partly broken so as to cancel the air-tightness of a space surrounded by the rear end cap 14, the circular tube body 12, and the gasket 19.

While this embodiment is described in combination with the connector 11, a liquid passage free of connector, as in Embodiment 1, may also be adopted.

Embodiment 4

Figure 13:
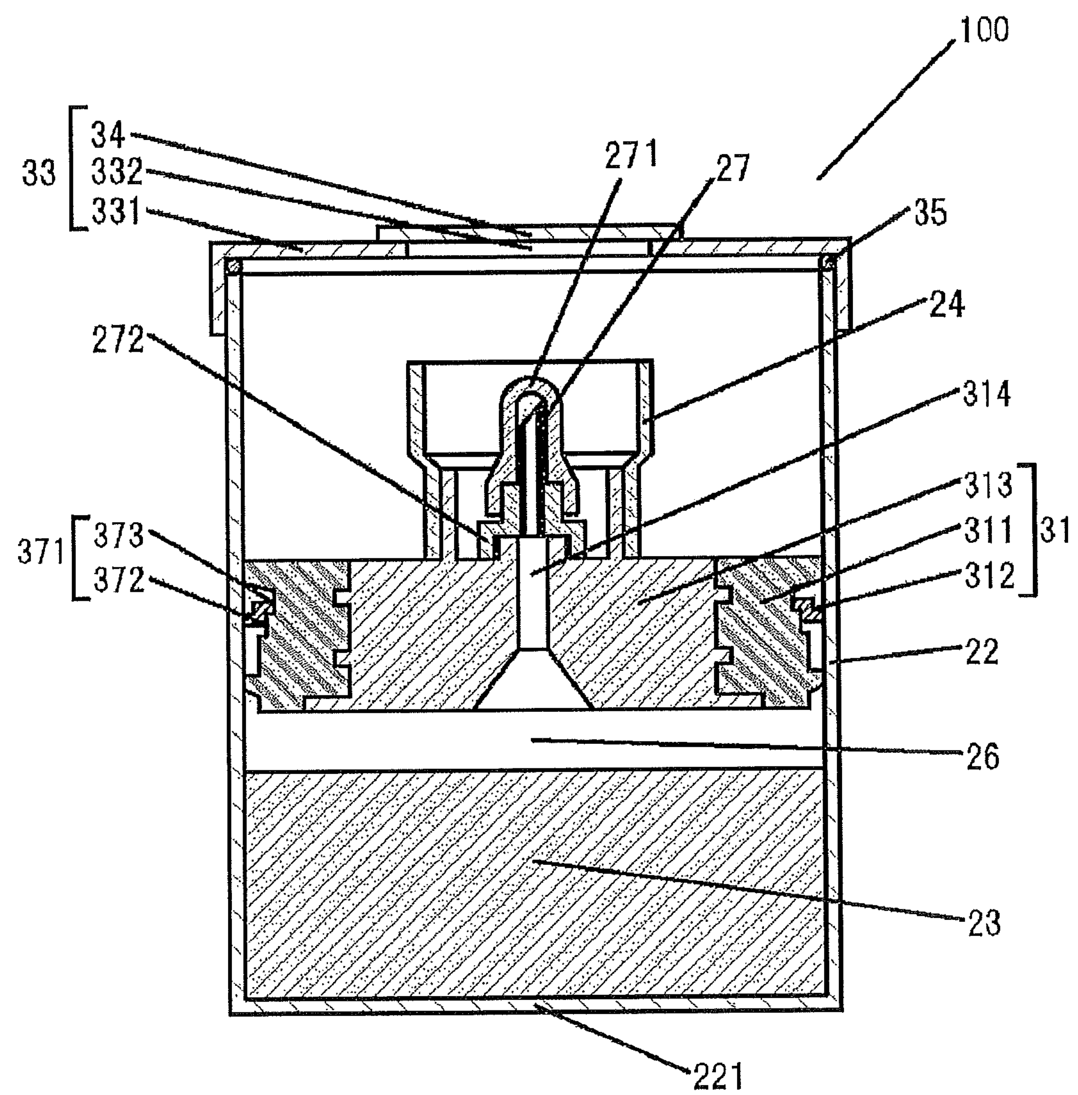
FIG. 13 is a sectional view of a powdery preparation container according to Embodiment 4 in the condition before connection.

FIG. 13 shows the first state of a powdery preparation container 100 which is an exemplary embodiment of the present invention.

The powdery preparation container 100 according to this embodiment includes a circular tube body 22 having a bottomed tubular shape, a gasket 31 which is fitted to the inside surface of the circular tube body 22 in an air-tight and liquid-tight manner and which can be slid inside the circular tube body along the longitudinal direction, a powdery preparation 23 contained in a space 26 surrounded by a bottom part 221 of the circular tube body 22 and the gasket 31, and a connecting portion 24 which is provided on the gasket 31 and to which a pipe body (prefilled syringe) preliminarily filled with a liquid preparation is detachably connected.

In addition, a tip opening portion of the circular tube body 22 is covered with sealing means 33. The sealing means 33 has a cap 331 fitted (mounted) to the tip opening portion of the circular tube body 22. Further, the cap 331 is formed with a cap opening 332 is disposed in its central portion. At the cap opening 332, a seat material 34 for sealing (closing) the cap opening 332 is disposed in an air-tight fashion. The seat material 34 is fixed to the upper side of the cap 331 by, for example, adhesion (adhesion by use of an adhesive or a solvent), and is peeled off from the cap 331 when the pipe body (prefilled syringe) prefilled with the liquid preparation is connected to the connecting portion 24. A packing 35 is disposed between the cap 331 and the tip opening portion of the circular tube body 22. The packing 35 is formed from an elastic material (e.g., a rubber material such as natural rubber), and is ring-like in overall shape. In addition, the packing 35 is circular in vertical sectional shape.

The gasket 31, specifically, has a form in which a rigid gasket body member 313 having a liquid passage 314 is fitted in a circular elastic gasket body member 311 and, further, an elastic ring member 312 is fitted on a large diameter part 372 of the elastic gasket body member 311.

Examples of material for the circular tube body 22 and the rigid gasket body member 313 in this embodiment include polypropylene, cyclic polyolefins, and polycarbonate.

In addition, examples of material for the elastic gasket body member 311 and the elastic ring member 312 include styrene-based elastomers, silicone rubbers, and butyl rubbers.

The volume of the space 26 is varied by movement of the gasket 31, and the inside of the space 26 is maintained at normal pressure in an unconnected condition where the pipe body is not yet connected to the connecting portion 24.

The liquid passage 314 is covered with a cover member 271 in the unconnected condition. Examples of a member to be connected to the liquid passage 314 include a needle pipe 27 connected to the liquid passage 314 through a needle hub 272, and the connector 11 used in Embodiment 3.

Connecting a prefilled syringe (not shown) to the connecting portion 24 and pushing the gasket 31 toward the bottom part 221 of the circular tube body 22 result in the second state in which the elastic ring member 312 is located on a small diameter part 373. In other words, the fitting force between the elastic ring member 312 and the inside surface of the circular tube body 22 is reduced, and the sliding resistance in sliding of the gasket 31 relative to the inside surface of the circular tube body 22 is reduced. Therefore, when a plunger of the syringe is pushed to cause the medical liquid in the syringe to flow into the powdery preparation container 100, the gasket 31 is easily slid toward the side of the opening of the circular tube body 22. Thereafter, a liquid preparation formed upon dissolution of the powdery preparation in the medical liquid can be easily recovered into the syringe, in which the medical liquid has been contained, by pulling the plunger.

When an embodiment is adopted in which the positional relationship between the large diameter part 372 and the small diameter part 373 of the elastic gasket body member 311 is reverse to the structure mentioned above, the second state can be obtained by pushing the plunger of the syringe. In this case, the operation can be performed without need to push the gasket 31 toward the side of the bottom part 221 of the circular tube body 22.

While a container for a powdery preparation has been described as an example in this embodiment, the medicine contained in the container may be any of various forms such as liquid preparation, powdery preparation, tablet, and jelly preparation, as in Embodiment 3. In the case where the medicine contained is a liquid preparation or a jelly preparation or the like, evaporation of the contained medicine to the exterior of the container can be prevented. In the case where the medicine contained is a powdery preparation, as in this embodiment, or tablets or the like, moistening of the medicine through penetration of moisture can be restrained.

In addition, while an embodiment in a normal-pressure condition as in Embodiment 1 has been described in this embodiment, a reduced-pressure condition may also be adopted.

Embodiment 5

Figure 7:
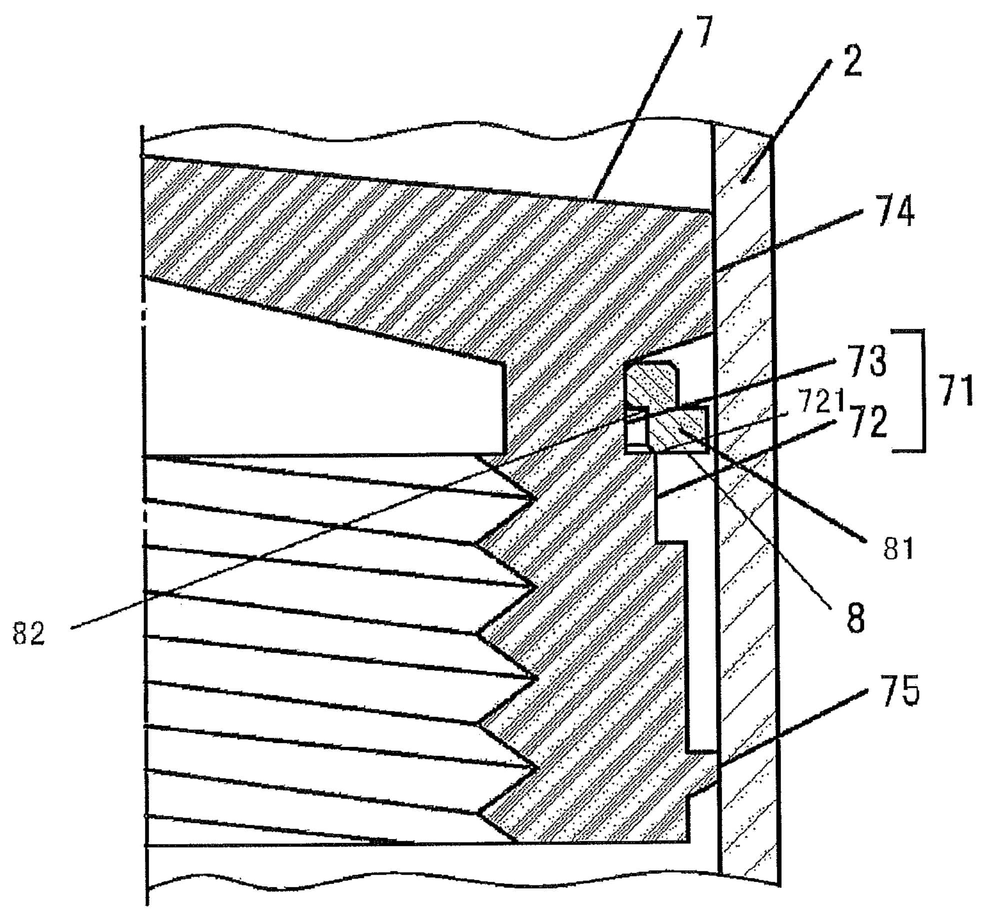
FIG. 7 is a sectional view showing the positional relationship between the gasket body member and the ring member according to Embodiment 1 when the liquid is injected and discharged (second state).
Figure 14:
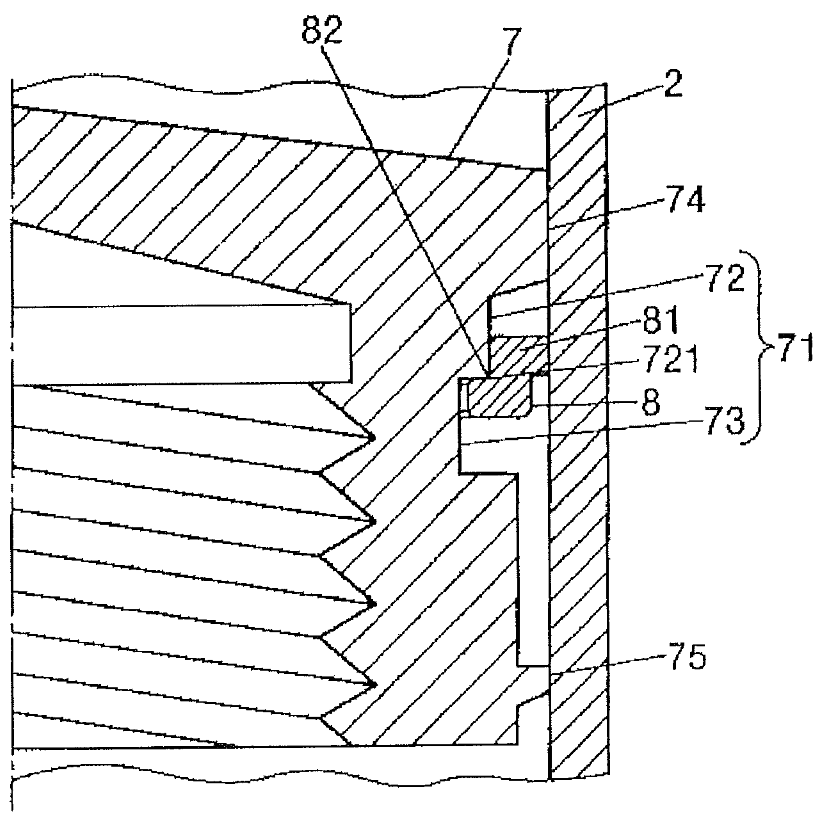
FIG. 14 is a sectional view showing the positional relationship between a gasket body member and a ring member in a prefilled syringe according to Embodiment 5 before liquid is injected and discharged (first state).
Figure 15:
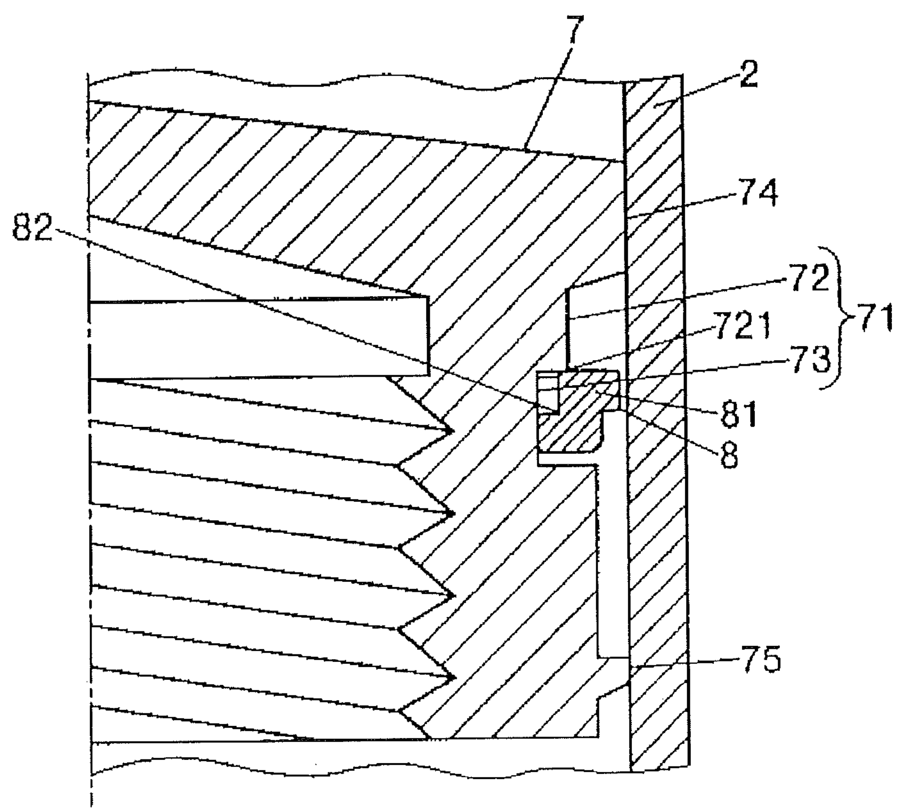
FIG. 15 is a sectional view showing the positional relationship between the gasket body member and the ring member in the prefilled syringe according to Embodiment 5 when the liquid is injected and discharged (second state).

FIG. 14 is a view (sectional view showing the positional relationship between a gasket body member and a ring member in a prefilled syringe according to Embodiment 5 before liquid is injected and discharged (first state)) corresponding to FIG. 6 in Embodiment 1, and FIG. 15 is a view (sectional view showing the positional relationship between the gasket body member and the ring member in the prefilled syringe according to Embodiment 5 when the liquid is injected and discharged (second state)) corresponding to FIG. 7.

Referring to these figures, Embodiment 5 will be described below. In the following, the explanation will focus on the difference from the above-described embodiments, and explanations of the same items as above will be omitted.

This embodiment is the same as Embodiment 1, except for a difference in the positional relationship of the large diameter part and the small diameter part.

As shown in FIGS. 14 and 15, a fitting portion 71 of a gasket body member 7 includes a large diameter part 72 on the distal side and a small diameter part 73 on the proximal side.

In the state shown in FIG. 14 (first state), an elastic ring member 8 is fitted on the large diameter part 72. In this state, sufficient air-tightness and liquid-tightness are maintained within the prefilled syringe 1, as mentioned above.

When an operation of pushing a plunger 7 in the direction toward the distal is performed starting from the state shown in FIG. 14, the elastic ring member 8 in the first state is not moved in the direction toward the distal relative to the circular tube body 2 as well as the gasket body member 7, but is released from the large diameter part 72 of the gasket body member 7. This ensures that the elastic ring member 8 is moved to the position of the small diameter part 73 and fitted onto the small diameter part 73, resulting in the second state.

In the second state, the sliding resistance in sliding of the gasket 3 relative to the circular tube body 2 is reduced as compared to the sliding resistance in the first state, so that injection and discharge of a medical liquid can be carried out smoothly, as mentioned above.

Further, the operation of pushing the plunger 7 in the direction toward the distal can serve also as, for example, an operation of removing bubbles from the inside of the prefilled syringe 1, in addition to the operation of canceling the fitting of the elastic ring member 8 on the large diameter part 72.

While the medical container according to the present invention has been described referring to the embodiments shown in the drawings, the invention is not limited to the embodiments. Each of the components of the medical container can be replaced by one having an arbitrary configuration which exhibits a function equivalent to the function of the original configuration. Further, arbitrary structures may be added.

In addition, the medical container according to the present invention may be one obtained by combining arbitrary two or more configurations (features) of the above-described embodiments.

INDUSTRIAL APPLICABILITY

The present invention provides a medical container including a gasket which has excellent air-tightness and liquid-tightness before liquid is injected and discharged and which has excellent slidability when the liquid is injected and discharged.

The invention claimed is:

1. A medical container comprising:

a circular tube body;

a cylindrical gasket sliding in the circular tube body in an air-tight and/or liquid-tight manner; and a liquid passage formed on a tip side through the circular tube body or the gasket, wherein the gasket is composed of a gasket body member having a cylindrical outside shape, and an elastic ring member fitted on the gasket body member, the gasket body member has a fitting portion for fitting in the elastic ring member, the fitting portion having a large diameter part and a small diameter part, an inside diameter of the elastic ring member is smaller than the large diameter part in a natural state, while an outside diameter of the elastic ring member is larger than an inside diameter of the circular tube body in a state where the elastic ring member is fitting on the large diameter part, and the elastic ring member is fitted onto the small diameter part in a second state by sliding the gasket in a longitudinal axial direction from a first state in which the elastic ring member is fitted on the large diameter part inside the circular tube body, wherein the elastic ring member has an engaging portion for engagement with a boundary portion between the large diameter part and the small diameter part in the first state.

2. The medical container according to claim 1, wherein in the first state, an outer circumferential portion of the elastic ring member and an inside surface of the circular tube body make contact with each other on a circumference.

3. The medical container according to claim 1, wherein fitting force between an outer circumferential portion of the elastic ring member and an inside surface of the circular tube body is greater in the first state than in the second state.

4. The medical container according to claim 1, wherein an outer circumferential portion of the gasket body member has at least one peak which extends continuously and makes contact with the circular tube body in an air-tight and/or liquid-tight manner.

5. The medical container according to claim 1, wherein an outside surface of the gasket body member and/or the inner circumference of the elastic ring member has been coated with a lubricant or subjected to a surface treatment.

6. The medical container according to claim 1, wherein sliding resistance between the elastic ring member and the gasket body member is smaller than sliding resistance between the elastic ring member and the circular tube body.

7. The medical container according to claim 1, wherein the large diameter part is located on an base end side relative to the small diameter part, and the elastic ring member in the first state is brought into the second state by movement of the gasket body member in a direction toward a base end relative to the circular tube body.

8. The medical container according to claim 1, wherein the large diameter part is located on a tip side relative to the small diameter part, and the elastic ring member in the first state is brought into the second state by movement of the gasket body member in a direction toward the tip relative to the circular tube body.

9. The medical container according to claim 1, wherein the elastic ring member has a portion which is compressed between the gasket body member and the circular tube body in the first state.

10. The medical container according to claim 1, wherein the elastic ring member is out of contact with the circular tube body in the second state.

11. The medical container according to claim 1, which is preliminarily filled with a medicine.

* * * * *